US007569746B2

(12) United States Patent
Bailey et al.

(10) Patent No.: US 7,569,746 B2
(45) Date of Patent: *Aug. 4, 2009

(54) METHOD FOR DELIVERY OF PROTEINS TO PLANT CELLS

(75) Inventors: Matthew A. Bailey, Des Moines, IA (US); Stanton B. Gelvin, West Lafayette, IN (US); Saikat Bhattacharjee, Ithaca, NY (US); William J. Gordon-Kamm, Urbandale, IA (US); Keith S. Lowe, Johnston, IA (US); Yumin Tao, Ames, IA (US)

(73) Assignees: Pioneer Hi-Bred International, Inc., Johnston, IA (US); Purdue Research Foundation, West Lafayette, IN (US)

( * ) Notice: Subject to any disclaimer, the term of this patent is extended or adjusted under 35 U.S.C. 154(b) by 318 days.

This patent is subject to a terminal disclaimer.

(21) Appl. No.: 10/913,202

(22) Filed: Aug. 6, 2004

(65) Prior Publication Data

US 2005/0015833 A1    Jan. 20, 2005

Related U.S. Application Data

(63) Continuation of application No. 09/570,319, filed on May 12, 2000, now Pat. No. 6,800,791, which is a continuation of application No. 09/316,914, filed on May 19, 1999, now abandoned.

(51) Int. Cl.
*C12N 15/09* (2006.01)
*C12N 15/82* (2006.01)
*A01H 5/00* (2006.01)

(52) U.S. Cl. ............... 800/294; 800/298; 800/288; 800/317.3; 800/320.1; 800/278; 435/430; 435/468; 435/431; 435/424; 435/428

(58) Field of Classification Search ............... None
See application file for complete search history.

(56) References Cited

U.S. PATENT DOCUMENTS 6,087,175 A    7/2000  John
6,800,791 B1 * 10/2004  Bailey et al. ............... 800/278

FOREIGN PATENT DOCUMENTS

WO    WO 98/41642    9/1998

OTHER PUBLICATIONS

Regensburg-Tuink, AJ et al (Nature (1993) 363: 69-71).*
Melchers et al (Plant Mol Biol Feb. 1990;14(2):249-59).*
Schramejer et al, 2003, Nucleic Acids Research, 31:860-868.*
DeVeylder et al., EMBL Database, Accession No. AJ000016 (1997).
DeVeylder et al., "The *Arabidopsis* Cks1At Protein Binds the Cyclin-dependent Kinases Cdc2aAt and Cdc2bAt," *FEBS Letters*, 1997, pp. 446-452, vol. 412(3).
Doonan et al., "Conserved and Novel Regulators of the Plant Cell Cycle," *Cell Biology*, 1997, pp. 824-830, vol. 9.
Ducommun et al., "Mutations at Sites Involved in Suc1 Binding Inactivate Cdc2," *Mol. Cell. Biol.*, Dec. 1991, pp. 6177-6184, vol. 11(12).
Herrerra-Estrella et al., "A Bacterial Peptide Acting as a Plant Nuclear Targeting Signal: The Amino-terminal Portion of *Agrobacterium* VirD2 Protein Directs a β-galactosidase Fusion Protein into Tobacco Nuclei," *Proc. Natl. Acad. Sci. USA*, Dec. 1990, pp. 9534-9537, vol. 87.
Hindley et al., "*Suc1* Encodes a Predicted 13-Kilodalton Protein That Is Essential for Cell Viability and Ise Directly Involved in the Division Cycle of *Schizosaccharomyces pombe*," *Mol. Cell. Biol.*, Jan. 1987, pp. 504-511, vol. 7(1).
John et al., "Association of the Plant $p34^{cdc2}$-like Protein with $p13^{suc1}$: Implications for Control of Cell Division Cycles in Plants," *Protoplasma*, 1991, pp. 70-74, vol. 161.
Melchers et al., "Octopine and Nopaline Strains of *Agrobacterium Tumefaciens* Differ in Virulence; Moelcular Characterization of the *virF* Locus," *Plant Molecular Biology*, 1990, pp. 249-259, vol. 14(2).
Patra et al., "Xc-p9, a *Xenopus* Suc1/Cks Homolog, has Multiple Essential Roles in Cell Cycle Control," *Genes & Development*, 1996, pp. 1503-1515, vol. 10.
Pines, "Reaching for a Role for the Cks Protein," *Current Biology*, 1996, pp. 1399-1402, vol. 6(11).
Regensburg-Tuink et al., "Transgenic *N. glauca* Plants Expressing Bacterial Virulence Gene *virF* are Converted into Hosts for Nopaline Strains of *A. tumefaciens*," *Nature*, May 6, 1993, pp. 69-71, vol. 363(6424).
Zhang et al., "At the Maize/*Agrobacterium* Interface: Natural Factors Limiting Host Transformation," *Chemistry & Biology*, 2000, pp. 611-621, vol. 7(8).

* cited by examiner

*Primary Examiner*—Medina A Ibrahim
(74) *Attorney, Agent, or Firm*—Alston & Bird LLP

(57) ABSTRACT

The invention relates to the use of a modified *Agrobacterium* to deliver proteins directly to plant cells. Proteins of interest are delivered to the plant host in the form of a fusion protein with the *Agrobacterium* virulence protein VirF. Nucleotide sequences encoding such fusion proteins of VirF and a protein of interest are provided. Also provided are bacteria modified to comprise such fusion proteins of VirF and a protein of interest. Methods of introducing such fusion proteins into a plant host are provided.

The invention finds use in facilitating plant transformation and particularly in the bio-engineering of desirable traits into crop plants.

13 Claims, No Drawings

SEQUENCE LISTING

```
<160> NUMBER OF SEQ ID NOS: 1

<210> SEQ ID NO 1
<211> LENGTH: 201
<212> TYPE: PRT
<213> ORGANISM: Agrobacterium tumefaciens

<400> SEQUENCE: 1

Met Arg Asn Ser Ser Leu Arg Asp Ala Ser Gly Ser Asn Asp Ala Gln
 1               5                  10                  15

Val Pro His Lys Thr Glu Leu Leu Asn Leu Pro Asp His Val Leu Thr
            20                  25                  30

Glu Val Ala Lys Arg Leu Ala Thr Asn Asn Pro Val Glu Ser Ala Glu
        35                  40                  45

Asn Ile Ala Asn Phe Ser Lys Ser His Arg Phe Thr Arg Asp Ala Val
    50                  55                  60

Arg Thr Glu Pro Leu Glu Lys Phe Ser Ser Arg Leu Lys Ile Ser Arg
65                  70                  75                  80

Asn Ala Lys Leu Leu Ser His Ala Val Arg His Ala Ala Thr Leu Pro
                85                  90                  95

Asp Gly Glu Gln Leu Ser Glu Ala Gln Leu Ser Gln Met Arg Ser Glu
            100                 105                 110

Val Ala Thr Arg Pro Val Leu Gly Val Ala Tyr Thr His Gln Asp Gly
        115                 120                 125

Gln Pro Glu Glu Arg Leu Ser Gly Asn His Leu Asp His Lys Ile Asn
    130                 135                 140

Asn Ile Pro Asn Leu Val Phe Asn Val Ala Glu Pro Ile Met Phe Asn
145                 150                 155                 160

Glu Ile Ser Ala Leu Glu Val Met Ala Glu Val Arg Pro Ile Ala Arg
                165                 170                 175

Ser Ile Lys Thr Ala His Asp Asp Ala Arg Ala Glu Leu Met Ser Ala
            180                 185                 190

Asp Arg Pro Arg Ser Thr Arg Gly Leu
        195                 200
```

METHOD FOR DELIVERY OF PROTEINS TO PLANT CELLS

CROSS-REFERENCE TO RELATED APPLICATIONS

This application is a continuation application of U.S. application Ser. No. 09/570,319, filed May 12, 2000, which is a continuation in part of U.S. application Ser. No. 09/316,914, filed May 19, 1999, both of which are incorporated herein by reference in their entirety.

FIELD OF THE INVENTION

The invention relates to delivering proteins to plant cells. More specifically, the invention provides methods and compositions to increase the efficiency of plant cell transformation and to engineer desirable plant traits through bacterial-mediated delivery of specific proteins into plants.

BACKGROUND OF THE INVENTION

Gene transfer has offered great promise in the genetic manipulation of organisms. The movement of genes within plant species has played an important role in crop improvement for many decades. The recombinant DNA methods which have been developed have greatly extended the sources from which genetic information can be obtained for crop improvement. A variety of methods have been developed for the transformation of plants and plant cells with DNA. Indeed, many of the recent advances in plant science have resulted from the power of recombinant DNA technology coupled with plant transformation. These approaches facilitate studies of the effects of specific gene alterations and additions on plant development and physiology. They also make possible the direct manipulation of genes to bio-engineer improved plant varieties.

While strides have been made in the genetic transformation of plants, it is by no means a routine matter. In fact, low transformation efficiencies preclude many genetic studies and commercial applications.

There is evidence to suggest that cells must be dividing for transformation to occur. It has been observed that dividing transformed cells represent only a fraction of cells that transiently express a transgene. Furthermore, the presence of damaged DNA in non-plant systems (similar to DNA introduced by particle gun or other physical means) has been well documented to rapidly induce cell cycle arrest (Siede, *Mutation Res.* 337(2):73-84). Therefore it would be desirable to provide a method for increasing the number of cells undergoing division.

Cell division in higher eukaryotes is controlled by two main checkpoints in the cell cycle that prevent the cell from entering either M- or S-phase of the cycle prematurely. Evidence from yeast and mammalian systems has repeatedly shown that over-expression of key cell cycle genes can either trigger cell division in non-dividing cells, or stimulate division in previously dividing cells (i.e. the duration of the cell cycle is decreased and cell size is reduced). Examples of genes whose over-expression has been shown to stimulate cell division include cyclins (see, e.g. Doerner et al.(1996) *Nature* 380:520-423; Wang et al., (1994) *Nature* 369:669-671; Quelle et al. (1993) *Genes Dev.* 7:1559-1571, E2F transcription factors (see, e.g. Johnson et al. (1993) *Nature* 365: 349-352; Lukas et al. (1996) *Mol. Cell. Biol.* 16:1047-1057), cdc25 (see, e.g. Bell et al. (1993) *Plant Mol. Biol.* 23:445-451; Draetta et al. (1996) BBA 1332:53-63), mdm2 (see, e.g. Teoh et al. (1997) *Blood* 90: 1982-1992.

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently expressing cells. Exacerbating this problem, the trauma that accompanies DNA introduction directs recipient cells into cell cycle arrest, and accumulating evidence suggests that many of these cells are directed into apoptosis or programmed cell death. (Bowen et al., *Tucson International Mol. Biol. Meetings*).

In addition to low transformation frequencies, in some cases the stable incorporation of DNA into recipient cells can be problematic. For example, the continuous expression of transformation enhancing genes can have negative consequences and transformed DNA may be incorporated into the host genome in a location that results in interference with other cellular functions.

The direct transfer of proteins to plant cells could be used to address both the issue of low transformation efficiencies and the undesirable effects of stable incorporation of transformed DNA. For example, a protein possessing transformation enhancing activity, that is delivered directly to a plant cell, would increase transformation efficiency and would only need to be present transiently.

Certain species of micro-organisms are known to transfer T-DNA into recipient cells by a mechanism similar to bacterial conjugation. The T-DNA traverses the bacterial membrane, the host cell wall and cell membranes, and the host nuclear membrane before integrating into the host genome through illegitimate recombination. Numerous bacterial proteins are included in these processes and have been characterized. Among these proteins are at least three from *Agrobacterium:* VirD2, VirE2, and VirF, whose genes are transcribed from the virulence region of the Ti plasmid, following which the proteins are transferred directly into plant cells.

VirD2 is a multifunctional protein which participates in the endonucleolytic cleavage of the T-DNA border sequences, the ligation of the left border nick for replacement strand synthesis, nuclear import of the T-complex, and precise integration of the 5' end of T-DNA into the host genome. VirD2 establishes a covalent association with the T-DNA between a specific right-border (RB) nucleotide and TYR-29 of the protein.

VirE2 encodes a multifunctional protein that has single-stranded DNA binding (SSB) activity and coats the T-strand. VirE2 is also likely to be involved both in nuclear import and with the integration of full-length T-DNA into the host genome. VirE2 is the most abundant of the virulence proteins with 350 to 700 copies thought to be required to coat a 20 kb T-strand.

The coding sequence of the virF gene is present in octopine strains but not in nopaline strains. The transfer of VirF protein to plant cells has not been directly shown, but has been inferred from the observation that transgenic *N. glauca* plants expressing bacterial virulence gene virF are converted into hosts for nopaline strains of *A. tumefaciens* (Regensburg-Tuink and Hooykaas (1993) *Nature* 363:69-71).

*Agrobacterium*-mediated transfer of proteins to plant cells in the form of virulence protein fusion constructs could be used to deliver proteins to plant cells to increase transformation efficiencies and to engineer specific desirable plant traits.

SUMMARY OF THE INVENTION

Methods and compositions are provided for the direct delivery of proteins into plant cells. Methods are provided for bacterial-mediated delivery of proteins to plant cells using *Agrobacterium* cells comprising nucleotide sequences encoding fusion proteins comprising a polypeptide of interest operably linked to the *Agrobacterium* virulence protein VirF. *Agrobacterium* cells are provided that are modified to comprise at least one fusion protein, such a fusion protein is expressed from a replicon or DNA construct comprising a virF coding sequence, or variant thereof, operably linked to a promoter that drives expression in a bacterium, wherein the polynucleotide encoding a VirF protein is operably linked to a polynucleotide encoding a polypeptide of interest.

The polynucleotide encoding the *Agrobacterium* VirF fusion is constructed on a replicon outside the T-DNA borders, so that the polynucleotide is not incorporated into the plant host genome upon infection of the plant cell with the modified bacterium. Thus, the problems associated with stable transformation of gene products into plant cells are avoided.

*Agrobacterium* fusion proteins are constructed to retain the functional properties of the VirF protein so that a selected protein as well as a transgene can be delivered to the same cell simultaneously.

This invention finds use in facilitating plant transformation and particularly in the bio-engineering of desirable plant traits into crop plants. Any protein or polypeptide may be utilized in the practice of the invention. Of particular interest are polypeptides that facilitate recombination, cell division, insertion of DNA into the genome, or other processes that aid in transformation.

DETAILED DESCRIPTION OF THE INVENTION

Definitions

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

By "T-DNA" is meant the T-DNA of an *Agrobacterium tumefaciens* Ti plasmid or from an *Agrobacterium rhizogenes* Ri plasmid, or a derivative thereof. The T-DNA may comprise an entire T-DNA, but need only comprise the minimal sequences required in cis for transfer (i.e., the right and the left T-DNA border sequences).

By "replicon" is meant any replicon (e.g., plasmid, vector or chromosome) that is capable of being maintained, preferably stably maintained, in any bacterial host of the *Rhizobiaceae* taxa. Such replicons include the *Rhizobiaceae* bacterium chromosome, plasmids, cosmids, phagemids, etc., derivatives thereof, and any other vector capable of replication in a *Rhizobiaceae* bacterium. For example, a binary vector suitable for both *Rhizobiaceae*-mediated transfer and for facile recombinant manipulations and replication in other organisms is useful in the methods and compositions of the invention. Preferably the replicon is a Ti or Ri plasmid or a derivative thereof.

As used herein "promoter" includes reference to a region of DNA upstream from the start of transcription and involved in recognition and binding of RNA polymerase and other proteins to initiate transcription.

The invention discloses novel methods of delivering proteins of interest directly to plant cells. Because the protein of interest is transferred directly into the plant cell, the potential negative effects which can result from the transient or stable introduction of genetic material are avoided. Another benefit of the invention is that a protein of interest can be directly delivered to a plant cell in conjunction with stable incorporation of a transgene. This allows for a broad range of utilities from increasing the efficiency of plant cell transformation to enhancing agroinfection.

The proteins of the invention are delivered from *Agrobacterium* into plant cells in the form of fusions with the *Agrobacterium* virulence protein VirF. Until the disclosure of this invention, the transfer of VirF protein to plant cells had not been directly shown, but had only been inferred from the observation that transgenic *N. glauca* plants expressing bacterial virulence gene virF are converted into hosts for nopaline strains of *A. tumefaciens*. Wild-type *N. glauca* plants are not known to be hosts for nopaline strains of *A. tumefaciens*.

The invention comprises methods for *Agrobacterium*-mediated delivery of a polypeptide of interest to a plant host in the form of a VirF fusion protein. The VirF fusions are constructed on a replicon outside of the T-DNA borders so that the nucleic acid is not incorporated in the genome of the host plant. The methods of the invention can be used to transfer any protein of interest to a plant cell. As VirF fusions are constructed outside of the T-DNA borders and in such a manner to retain both those properties of VirF required to mediate delivery into plant cells and the selected activity required for altering cell function, this method is also useful for co-delivery of T-DNA and the functional selected protein into the same host cell.

The *Agrobacterium*-mediated transfer of proteins to plant cells through VirF fusions is not dependent on transfer of T-DNA, and can be constructed on replicons or constructs not containing T-DNA borders. While protein transfer to a plant cell may be improved by the presence of a Ti plasmid in an *Agrobacterium* cell of the invention, the methods of the invention do not depend on the presence of a Ti plasmid in the *Agrobacterium* cell.

An embodiment of the invention utilizing simultaneous co-delivery of T-DNA and the functional selected protein into the same host cell involves the delivery of a VirF-"cell cycle protein" fusion. Genes which are involved in the regulation of or can influence cell cycle division in plants are known in the art. Examples include cyclins (Doerner (1994) *Plant Physiol.* 106:823-827.), maize cdc2 (Colasanti et al. (1991) *PNAS* 88:3377-3381), cdc25+ (Russell and Nurse (1986) *Cell* 45:145-153), the gemini virus RepA gene (U.S. Ser. No. 09/257, 131), plant E2F (Ramirez-Parra et al. (1999) *Nuc. Ac. Res.* 27:3527-3533 and Sekine et al. (1999) *FEBS Lett.* 460:117-122), the IPT gene of *Agrobacterium tumefaciens* (Strabala et al. (1989) *Mol. Gen. Genet.* 216:388-394, Bonnard et al. (1989) *Mol Gen. Genet.* 216:428-438, DDBJ/EMBL/GenBank), TZS (Beaty et al. (1986) *Mol. Gen. Genet.* 203:274-280, Akiyoshi et al. (1985) *Nucleic Acids Res.* 13:2773-2788, Regier et al. (1989) *Nucleic Acids Res.* 17:8885), CKI1 (Kakimoto (1996) *Science* 274:982-985) and PSK-α (Yang et al. (1999) *PNAS* 96:13560-13565), all of which are incorporated herein by reference. The promotion of cell division by the transient presence of selected cell cycle proteins may enhance integration of the coresident T-DNA.

In addition, the methods of the invention can be used to test the efficacy of visible selectable markers by transferring VirF fusions with proteins such as GFP (Haseloff et al (1995) *Trends Genetics* 11:328-329), GUS (beta-Glucoronidase), and Luciferase, (Visser et al. (1985) *Biochemistry* 24:1489-

1496). The visible markers could also be used in the system to test changes in protocols that would enhance transfer of molecules to various plant cells, or cells or tissues of recalcitrant species.

Using methods of the invention with selected proteins such as Bcl-2 (Pedoraro et al. (1984) *Proc. Nat. Ac. Sci.* 81 (22): 7166-7170 or IAP (inhibitor of apoptosis) (Crook et al. (1993) *Journ. Vir.* 67(4):2168-2174) would reduce the tendency of recently transformed cells to undergo programmed cell death, and in the process increase transgene integration and overall transformation frequencies.

Fusing the polynucleotide encoding the delivery protein VirF to genes such as fus3 (Elion et al. (1990) *Cell* 60(4):649-664), LEC1 (Lotan et al. (1998) *Cell* 93:1195-1205), CLAVATA, WUSCHEL, or Zwille (Clark et al. (1996) *Development* 122:1567-1575, Schoof et al. (2000) *Cell* 100:635-644, Mayer et al. (1998) *Cell* 95:805-815, Endrizzi et al. (1996) *Plant J* 10:967-979), pk1 (Ogas et al. (1997) *Science* 277:91-94) KNOTTED-1 (Lowe et al. (1992) *Genetics* 132: 813-822, Vollbrecht et al. (1991) *Nature* 350:24-243), kn1 family members including Rs1 (Schneeberger et al. (1995) *Genes Dev.* 9:2292-2304), Lg3 (Muehlbauer et al. (1999) *Plant Physiol.* 119:651-662), OSH1 (Matsuoka et al. (1993) *Plant Cell* 5:1039-1048), OSH15 (Sato et al. (1998) *Plant Mol. Biol.* 38:983-998), OSH71 (DDBJ/EMBL/GenBank Accession #Ab028885), SbH1 (Ma et al. (1994) *Plant Mol. Biol.* 24:465-473), STM (Long et al. (1996) *Nature* 379:66-69), HvKNOX3 (Meuller et al. (1995) *Nature* 347:727-730) or KNAT1 (Lincoln et al. (1994) *Plant Cell* 6:1859-1876) would commit cells and cell lineages to a desired developmental fate such as meristem or embryo development. In addition to those described above, there are a number of other Kn1 family members that can be used similarly and are reviewed in Bharathan et al. (1999) *Mol. Biol. Evol.* 16:553-563. All of the above are incorporated herein by reference.

Another embodiment of the invention is to use it to directly deliver a recombinase protein to a plant cell for use with a site-specific recombinase protein system such as FLP (U.S. patent application Ser. No. 08/972,258) or Cre/loxP (Abremski-K. et al. (1985) *Jour. Mol. Bio.* 184(2):211-220) to catalyze a variety of recombination-mediated alterations. Some examples of recombination-mediated alterations are removal of one transgene and activation of a second, integration of a transgene, gene replacement and genomic exchanges. In this embodiment, a modified *Agrobacterium* containing a VirF-recombinase fusion protein can be used to transfer T-DNA containing a DNA of interest flanked by directly repeated target sites for a site specific recombinase. The VirF-recombinase fusion protein in the plant cell can catalyze the incorporation of the DNA of interest into the plant genome.

By "site-specific recombinase" is meant any enzyme capable of being functionally expressed in plants, that catalyzes conservative site-specific recombination between its corresponding target sites. By "target site for a site-specific recombinase" is meant a DNA sequence that is recognized by a particular site-specific recombinase. A variety of target sites are known to those skilled in the art and may be used in the methods and compositions of the invention. The site may have the sequence of the cognate site for a given recombinase, or may be modified, so long as it is capable of acting as a target site. The site may contain the minimal sequences necessary for recombination, or it may contain additional sequences that enhance recombination.

In another embodiment, an *Agrobacterium* modified to contain a VirF-recombinase fusion protein could be used to facilitate the known method of *Agrobacterium*-meditated introduction of a virus to a plant host. This method of *Agrobacterium*-meditated introduction of a virus to a plant host is known as agroinfection (for a review, see Grimsley, pp. 325-342, in *Methods in Molecular Biology*, vol 44: *Agrobacterium Protocols*, ed. Gartland and Davey, Humana Press, Inc., Totowa, N.J.; and Grimsley (1990) *Physiol. Plant.* 79:147-153). Agroinfection has been reported in a number of publications as a successful method for inducing systemic viral infections in plant cells, including monocotyledonous plants such as maize (Heath et al. (1997) *Mol. Plant-Microbe Interact.* 10:221-227, Grimsley et al. (1989) *Mol. Gen. Genet.* 217:309-316). In many instances, particularly when naked viral nucleic acid is non-infectious, agroinfection is the only way of transforming a plant with cloned viral DNA. Even where naked viral nucleic acid is infectious, agroinfection is frequently used because it is relatively efficient and does not require the production of large amounts of plasmid or viral DNA.

In the method of agroinfection, *Agrobacterium* is used to mediate the viral infection of plants by inserting a viral genome into the T-DNA. Following transfer of the T-DNA to the plant cell, excision of the viral genome from the T-DNA (mobilization) is required for successful viral infection.

U.S. Pat. No. 6,300,545 entitled "Mobilization of Viral Genomes From T-DNA Using Site-Specific Recombination Systems", the contents of which are incorporated herein by reference, describes a method for the facilitation of agroinfection through expression of a recombinase protein in the plant being infected. In this method the *Agrobacterial* T-DNA contains a viral replicon flanked by directly repeated target sites for a site-specific recombinase and, optionally, a DNA of interest linked to the viral replicon. The recombinase is provided to plant cells by expression from a polynucleotide operably linked to a promoter driving expression in a plant cell. Expression of the site-specific recombinase results in the excision of the viral replicon and the associated DNA of interest. The viral replicon and DNA of interest are then replicated to high copy number in the host plant cell.

In the present invention, a modified *Agrobacterium* containing a VirF-recombinase fusion protein is used to transfer to a plant host T-DNA containing a viral replicon flanked by directly repeated target sites for a site specific recombinase and optionally a DNA of interest linked to the viral replicon. More specifically, by "modified bacterium" is intended a bacterium that contains a replicon comprising a polynucleotide encoding VirF, or a variant thereof, operably linked to a promoter for expression in bacteria, that is operably linked to a polynucleotide encoding a polypeptide of interest. The presence of the VirF-recombinase fusion protein in the plant cell results in the excision of the viral replicon and the associated DNA of interest. The viral replicon and DNA of interest are then replicated to high copy number in the host plant cell. In this case, the DNA encoding the recombinase is not incorporated into the host plant genome. Furthermore, this method ensures a high frequency of simultaneous co-delivery of T-DNA and the VirF-recombinase protein into the same host cell.

Site-specific recombinases useful in the methods and compositions of the invention include recombinases from the integrase and resolvase families, variants thereof, and any other naturally occurring or recombinantly produced variant thereof, that catalyzes conservative site-specific recombination between specified DNA sites. By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, in that they continue to possess the desired biological activity of the native protein. Such variants may result from, for example, genetic polymorphism or from human manipulation.

The integrase family of recombinases has over thirty members and includes FLP, Cre, Int and R. The resolvase family includes γδ resolvase. Recombinant enzymes that catalyze site-specific conservative recombination include moFLP, described in U.S. Pat. No. 5,929,301, and moCre, Preferably, the recombinase is one that does not require cofactors or a supercoiled substrate. Such recombinases include Cre, FLP moFLP, and moCre.

The FLP recombinase gene from yeast (*Saccharomyces cerevisiae*) is commercially available in plasmid pOG44 from Stratagene Cloning Systems (11011 North Torrey Pines Road, La Jolla, Calif. 92037). Similarly, the sequences of many other site specific recombinases and their cognate target sites are publicly or commercially available.

Proteins delivered to plant cells using the *Agrobacterium*-mediated method will generally be localized to the nucleus of the plant cell. Additional modifications to the protein could result in the targeting to other specific subcellular locations within the plant cell. For example, "signal" or "transit" peptides capable of targeting a polypeptide to the chloroplast, mitochondrian, or vacuole are known in the art. It is recognized that in the *Agrobacterium*-mediated method of protein delivery to plant cells, the signal peptide would be added to the polypeptide of interest in the bacterium. More specifically, the modified *Agrobacterium* containing a replicon encoding VirF operably linked to a polynucleotide encoding a polypeptide of interest, will additionally contain a nucleic acid encoding a transit peptide to target the polypeptide of interest to a specific subcellular location.

Known chloroplast transit peptides include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-enolpyruvyl)shikimate-3-phosphate synthase (EPSPS) (Archer et al. (1990) *J Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

*Agrobacterium* fusion proteins could similarly be targeted to the mitochondrian or vacuole through the use of signal peptides. For a review of protein targeting to the mitochondrian, see Rapoport et al. (1999) *Biol Chem* 380:1143-1150; Claros et al. (1997) *Curr Opin Struct Biol* 7:394-398; Shore et al. (1995) *Eur J Biochem* 227:9-18; von Heijne (1994) *Subcell Biochem* 22:1-19; and Schwarz and Neupert (1994) *Biochim Biophys Acta* 1187:270-274. Reviews involving protein targeting to the vacuole are Nakamura and Matsuoka (1993) *Plant Physiol* 101:1-5; Vitale and Chrispeels (1992) *Bioessays* 14:151-160; and Chrispeels and Raikel (1992) *Cell* 68:613-616.

The method of *Agrobacterium*-mediated protein delivery to plant cells could also be extended to employ multiple VirF protein fusions on the same, or coresident replicons. This would conceivably allow the transient activity of groups of proteins capable of mediating complex functions or pathways related to transformation objectives.

This *Agrobacterium* strategy is potentially simpler than current methods for the direct delivery of proteins to plant cells. For example, delivery of a polypeptide of interest to plant cells using the method of bombardment requires expression and isolation of the polypeptide. In contrast, the *Agrobacterium* method described in this application does not require protein purification and avoids the potential problems associated with the presence of contaminating polypeptides.

The present invention may be used for delivery of proteins to any plant species, including, but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

As used herein, the term "plant" includes reference to whole plants, plant organs (e.g., leaves, stems, roots, etc.), seeds and plant cells and progeny of same. Plant cell, as used herein includes, without limitation, plant cells within or isolated from seeds, suspension cultures, embryos, meristematic regions, callus tissue, leaves, roots, shoots, gametophytes, sporophytes, pollen, and microspores.

*Agrobacterium tumefaciens*-mediated transformation techniques are well described in the scientific literature. See, for example Horsch et al. (1984) *Science* 233: 496-498, Fraley et al. (1983) *Proc. Natl. Acad. Sci.* 80: 4803, and Kado (1991) *Crit. Rev. Plant Sci.* 10:1. Descriptions of the *Agrobacterium* vector systems and methods for *Agrobacterium*-mediated gene transfer are provided in Gruber et al. supra, Miki et al. supra, and Moloney et al. (1989) *Plant Cell Reports* 8:238. Although *Agrobacterium* is useful primarily in dicots, certain monocots can be transformed by *Agrobacterium*. For instance, *Agrobacterium* transformation of maize is described in U.S. Pat. No. 5,981,840. Other methods of agroinfection include *Agrobacterium rhizogenes*-mediated transformation (see, e.g., Lichtenstein and Fuller In: *Genetic Engineering*, vol. 6, PWJ Rigby, Ed., London, Academic Press, 1987; and Lichtenstein and Draper In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16.

Optimized methods and vectors for *Agrobacterium*-mediated transformation of plants in the family Graminae, such as rice and maize have been described in Heath et al. (1997) *Mol. Plant-Microbe Interact.* 10:221-227; Hiei et al. (1994) *Plant J.* 6:271-282 and Ishida et al. (1996) *Nat. Biotech.* 14:745-750, the contents of which are incorporated herein by reference. The efficiency of maize transformation is affected by a variety of factors including the types and stages of tissue infected, the concentration of *Agrobacterium*, the tissue culture media, the Ti vectors and the maize genotype. Super binary vectors carrying the vir genes of *Agrobacterium* strains A281 and A348 are useful for high efficiency transformation of monocots. However, even without the use of high efficiency vectors, it has been demonstrated that T-DNA is transferred to maize at an efficiency that results in systemic infection by viruses introduced by agroinfection, although tumors are not formed (Grimsley et al. (1989) *Mol. Gen. Genet.* 217:309-316). This is because integration of the T-DNA containing the viral genome is not required for viral multiplication, since the excised viral genome acts as an independent replicon.

Another useful basic transformation protocol involves a combination of wounding by particle bombardment, followed by use of *Agrobacterium* for DNA delivery, as described by Bidney et al. (1992) *Plant Mol. Biol.* 18:301-313. In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with selection agents.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime (plus selection agents).

The regeneration of plants from leaf explants subsequent to infection with a modified *Rhizobiaceae* bacterium can be achieved as described by Horsch et al. (1985) *Science* 227: 1229-1231. In this procedure, transformants are grown in the presence of a selection agent and in a medium that induces the regeneration of shoots in the plant species being transformed as described by Fraley et al. (1983) *Proc. Natl. Acad. Sci. U.S.A.* 80:4803. This procedure typically produces shoots within two to four weeks and these transformant shoots are then transferred to an appropriate root-inducing medium containing the selective agent and an antibiotic to prevent bacterial growth.

Regeneration can also be obtained from plant callus, explants, organs, or parts thereof. Such regeneration techniques are described generally in Klee et al. (1987) *Ann. Rev. of Plant Phys.* 38: 467-486. The regeneration of plants from either single plant protoplasts or various explants is well known in the art. See, for example, *Methods for Plant Molecular Biology*, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, 3$^{rd}$ edition, Sprague and Dudley Eds., American Society of Agronomy, Madison, Wis. (1988).

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

EXPERIMENTAL

EXAMPLE 1

*Agrobacterium tumefaciens*-Mediated Delivery of a VirF-GUS Fusion Protein to Tobacco and *Arabidopsis* Cells To demonstrate that VirF from *Agrobacterium tumefaciens* can function to deliver proteins to plant cells, the polynucleotide encoding VirF was operably linked to a polynucleotide encoding the reporter protein β-glucuronidase (GUS). A virF-gusA (also virF-uidA) fusion construct was placed on a replicon not containing T-DNA borders that would replicate in *Agrobacerium tumefaciens*. In the replicon the polynucleotides encoding VirF and GUS were operably linked. This construction was placed under the control of the virF promoter and, consequently, should be regulated by the virA/virG genes as part of the phenolic-induced vir regulon. The replicon was introduced into the wild-type octopine strain *A. tumefaciens* A348. Expression of the virF-gusA fusion construct in *Agrobacterium* was found to be somewhat independent of acetosyringone (AS) induction. However, even with the incomplete AS dependence, induction of VirF-GUS expression by AS was increased significantly in *Agrobacterium*, as measured by GUS fluorimetric analyses.

The bacterial strain *A. tumefaciens* A348 containing the virF-gusA fusion construct was incubated overnight in AS-induction medium and used to infect suspension cell cultures of tobacco (BY-2) and *Arabidopsis thaliana* (ecotype Ws) at a bacterial/plant cell ratio of approximately 1000:1. After 24 hours, the plant cells were washed and the medium replaced with medium containing timentin to kill *Agrobacterium*. Cell growth was continued for several more days, and cells were assayed initially 2 days after the start of co-cultivation. GUS enzyme activity was observed (measured by blue staining of the plant cells using the chromogenic dye X-gluc) in both tobacco and *Arabidopsis* cells. GUS was transferred to over 90% of the plant cells as indicated by the chromogenic staining. These results indicate that *Agrobacterium tumefaciens* is able to transfer VirF fusion proteins to plant cells and that this transfer is independent of transfer of T-DNA.

EXAMPLE 2

Delivery of a VirF-GUSA Fusion Protein to Tobacco and *Arabidopsis* Cells by *Agarobacterium tumefaciens* virA and virG Mutant Strains The virF-gusA replicon was introduced into several *Agrobacterium* strains containing mutations in the virA and virG genes and used to infect tobacco and *Arabidopsis* cells as described in Example 1. The VirF-GUSA fusion protein was transferred to the plant cells by the mutant *Agrobacterium* strains as GUS staining was detected in the co-cultivated plant cells. These results suggest that the virB/virD4-encoded T-pilus is not necessary for VirF fusion protein transfer to plant cells.

EXAMPLE 3

Delivery of a VirF-GUSA Fusion Protein to Tobacco and *Arabidopsis* Cells by *Agrobacterium tumefaciens* virB and virD Mutant Strains The virF-gusA replicon was introduced into two avirulent *A. tumefaciens* strains harboring different polar virB mutations, and a polar virD mutation. These avirulent *A. tumefaciens* strains were then used to infect tobacco and *Arabidopsis* cells as described in Example 1 to test the hypothesis that the virB/virD4-encoded T-pilus is not necessary for VirF-GUS fusion protein transfer to plant cells. Each of these mutant strains was also able to transfer VirF-GUS protein to plant cells. These results are direct confirmation that the T-pilus is not necessary for VirF fusion protein transfer to plant cells.

EXAMPLE 4

Delivery of a VirF-GUSA Fusion Protein to Tobacco and *Arabidopsis* Cells by an *Agrobacterium tumefaciens* virE Mutant Strain The virF-gusA replicon was introduced into a polar virE mutant *A. tumefaciens* strain and used to infect tobacco and *Arabidopsis* cells as described in Example 1. GUS staining was detected in the co-cultivated plant cells, indicating that the VirF-GUSA fusion protein was transferred to the plant cells by this mutant *Agrobacterium* strain. These results indicate that a functional VirE protein is not necessary for VirF fusion protein transfer to plant cells.

EXAMPLE 5

Delivery of a VirF-GUSA Fusion Protein to Tobacco and *Arabidopsis* Cells by an *Agrobacterium tumefaciens* Strain Lacking a T-DNA Region The virF-gusA replicon was introduced into *A. tumefaciens* strain (GV3101) which lacks a T-DNA region. This strain was then used to infect tobacco and *Arabidopsis* cells as described in Example 1. GUS staining was detected in the co-cultivated plant cells, indicating that the VirF-GUSA fusion protein was transferred to the plant cells by this T-DNA deficient *Agrobacterium* strain. These results indicate that transfer of a VirF fusion protein to a plant cell is independent of T-DNA transfer to a plant cell.

EXAMPLE 6

Delivery of a VirF-GUSA Fusion Protein to Tobacco and *Arabidopsis* Cells by an *Agrobacterium tumefaciens* Strain Lacking a Ti-Plasmid The virF-gusA replicon was introduced into *A. tumefaciens* strain (A136) which lacks a Ti-plasmid. This strain was then used to infect tobacco and *Arabidopsis* cells as described in Example 1. GUS staining was detected in the co-cultivated plant cells, although at low levels, indicating that the VirF-GUSA fusion protein was transferred, at low efficiency, to the plant cells by this Ti-plasmid deficient *Agrobacterium* strain. These results indicate that the presence of a Ti-plasmid is not necessary for *Agrobacterium*-mediated transfer of a VirF fusion protein to a plant cell.

EXAMPLE 7

*Agrobacterium*-Mediated Transformation of Maize

For *Agrobacterium*-mediated transformation of maize, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of infecting at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. An optional "resting" step follows the co-cultivation period. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for delivering a polypeptide of interest to a plant cell, said method comprising infecting a plant cell with an *Agrobacterium* which comprises a polynucleotide fusion construct comprising a VirF fusion polynucleotide operably linked to a promoter which drives expression in *Agrobacterium,* wherein the VirF fusion polynucleotide comprises a VirF polynucleotide operably linked to a polynucleotide encoding a polypeptide of interest, wherein expression of said VirF fusion polynucleotide produces a VirF fusion polypeptide, wherein said polypeptide of interest is delivered to said plant cell, and wherein said polynucleotide fusion construct is not incorporated into the plant cell genome.

2. The method of claim 1 wherein said plant cell is a corn, soybean, sorghum, wheat, rice, alfalfa, sunflower, or *Brassica* sp. cell.

3. The method of claim 1 wherein said polypeptide of interest is a selectable marker protein.

4. The method of claim 3 wherein said selectable marker protein is a visible selectable marker protein.

5. The method of claim 3 wherein said selectable marker is β-Glucuronidase, Green Fluorescent Protein or Luciferase.

6. The method of claim 1 wherein said polynucleotide fusion construct further comprises an operably linked polynucleotide encoding a transit polypeptide sequence, wherein said transit polypeptide sequence targets said VirF fusion polypeptide to a subcellular organelle other than the nucleus.

7. The method of claim 6 wherein said subcellular organelle is a chloroplast.

8. The method of claim 1 wherein said *Agrobacterium* is a mutant *Agrobacterium tumefaciens* strain comprising a mutation in one or more of a virA, virG, virB, virD or virE gene.

9. The method of claim 1 wherein said *Agrobacterium* is an *Agrobacterium tumefaciens* mutant strain lacking at least one of the group consisting of a Ti plasmid and a T-DNA region.

10. The method of claim 1 wherein said plant cell is a monocot.

11. The method of claim 1 wherein said plant cell is a dicot.

12. The method of claim 1 wherein said plant cell is sunflower or *Brassica* sp.

13. The method of claim 1 further comprising growing the plant cell to produce a plant.

* * * * *

UNITED STATES PATENT AND TRADEMARK OFFICE
CERTIFICATE OF CORRECTION

PATENT NO. : 7,569,746 B2  Page 1 of 1
APPLICATION NO. : 10/913202
DATED : August 4, 2009
INVENTOR(S) : Bailey et al.

It is certified that error appears in the above-identified patent and that said Letters Patent is hereby corrected as shown below:

Column 7,

Line 11, after "moCre," insert --described in the provisional application entitled, "An Artificial Site-Specific DNA Recombinase With Specificities to Multiple Recombination Target Sites".--.

Column 11,

Line 23, "Agarobacterium" should read --Agrobacterium--.

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO.        : 7,569,746 B2                                   Page 1 of 1
APPLICATION NO.   : 10/913202
DATED             : August 4, 2009
INVENTOR(S)       : Bailey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this

Seventh Day of September, 2010

David J. Kappos
*Director of the United States Patent and Trademark Office*